US00PP31493P3

(12) United States Plant Patent
van Langen

(10) Patent No.: US PP31,493 P3
(45) Date of Patent: Feb. 25, 2020

(54) ***ECHEVERIA* PLANT NAMED 'AMIECH1819'**

(50) Latin Name: ***Echeveria* hybrid**
Varietal Denomination: AMIECH1819

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 16/501,051

(22) Filed: Feb. 13, 2019

(65) Prior Publication Data

US 2019/0281749 P1 Sep. 12, 2019

(30) Foreign Application Priority Data

Mar. 8, 2018 (QZ) ..... PBR 2018/0705

(51) Int. Cl.
*A01H 5/12* (2018.01)
*A01H 6/00* (2018.01)
*A01H 6/32* (2018.01)

(52) U.S. Cl.
USPC ..... Plt./373
CPC ..... *A01H 6/00* (2018.05); *A01H 5/12* (2013.01); *A01H 6/32* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Echeveria* plant named 'AMIECH1819' which is characterized by narrow obovate to near spatulate succulent foliage with a moderately to strongly convex and moderately to strongly revolute to near-tubular aspect, foliage with a conspicuous irregularly globular growth on the abaxial surface, heavily glaucous juvenile foliage at the center of the rosette which generally appears to be mauve colored and margined pink, moderately glaucous mature foliage towards the outer whorls of the rosette which is greyed-green and margined greyed-red, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'AMIECH1819'.

CROSS REFERENCE TO RELATED APPLICATIONS

This application claims priority to the Community Plant Variety Rights application number 2018/0705, filed Mar. 8, 2018, which is herein incorporated by reference.

BACKGROUND OF THE INVENTION

Parentage: 'AMIECH1819' is a naturally-occurring, partial-plant mutation of *Echeveria* 'Perle Von Nurnberg' (not patented) which was discovered by the inventor at a commercial greenhouse in Heerhugowaard, the Netherlands. In the summer of 2014, the inventor observed one leaf growing on a 'Perle Von Nurnberg' plant which exhibited a moderately to strongly convex and moderately to strongly revolute to near-tubular aspect with an irregularly globular growth present on the abaxial surface. The leaf was harvested from the plant, rooted, and grown to a mature size in order to confirm the distinctness and stability of the characteristics first observed. In the summer of 2015, upon confirmation of distinctness and stability, 'AMIECH1819' was selected for commercialization.

Asexual Reproduction: Asexual reproduction of the new cultivar 'AMIECH1819', by way of rooting leaf cuttings, was first initiated in the summer of 2016 at the inventor's commercial greenhouse in Heerhugowaard, the Netherlands. Through four subsequent generations, the unique features of this cultivar have proven to be stable and true to type.

SUMMARY OF THE INVENTION

The cultivar 'AMIECH1819' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1819'. These characteristics in combination distinguish 'AMIECH1819' as a new and distinct *Echeveria* cultivar:

1. 'AMIECH1819' exhibits narrow obovate to near spatulate succulent foliage arranged in a stemless basal rosette; and
2. 'AMIECH1819' exhibits foliage with a moderately to strongly convex and moderately to strongly revolute to near-tubular aspect; and
3. 'AMIECH1819' exhibits a conspicuous irregularly globular growth on the abaxial surface of the foliage; and
4. 'AMIECH1819' exhibits heavily glaucous juvenile foliage at the center of the rosette which generally appears to be mauve colored and margined pink; and 5. 'AMIECH1819' exhibits moderately glaucous mature foliage towards the outer whorls of the rosette which is greyed-green and margined greyed-red.

BOTANICAL DESCRIPTION OF THE PLANT

Figure 1:
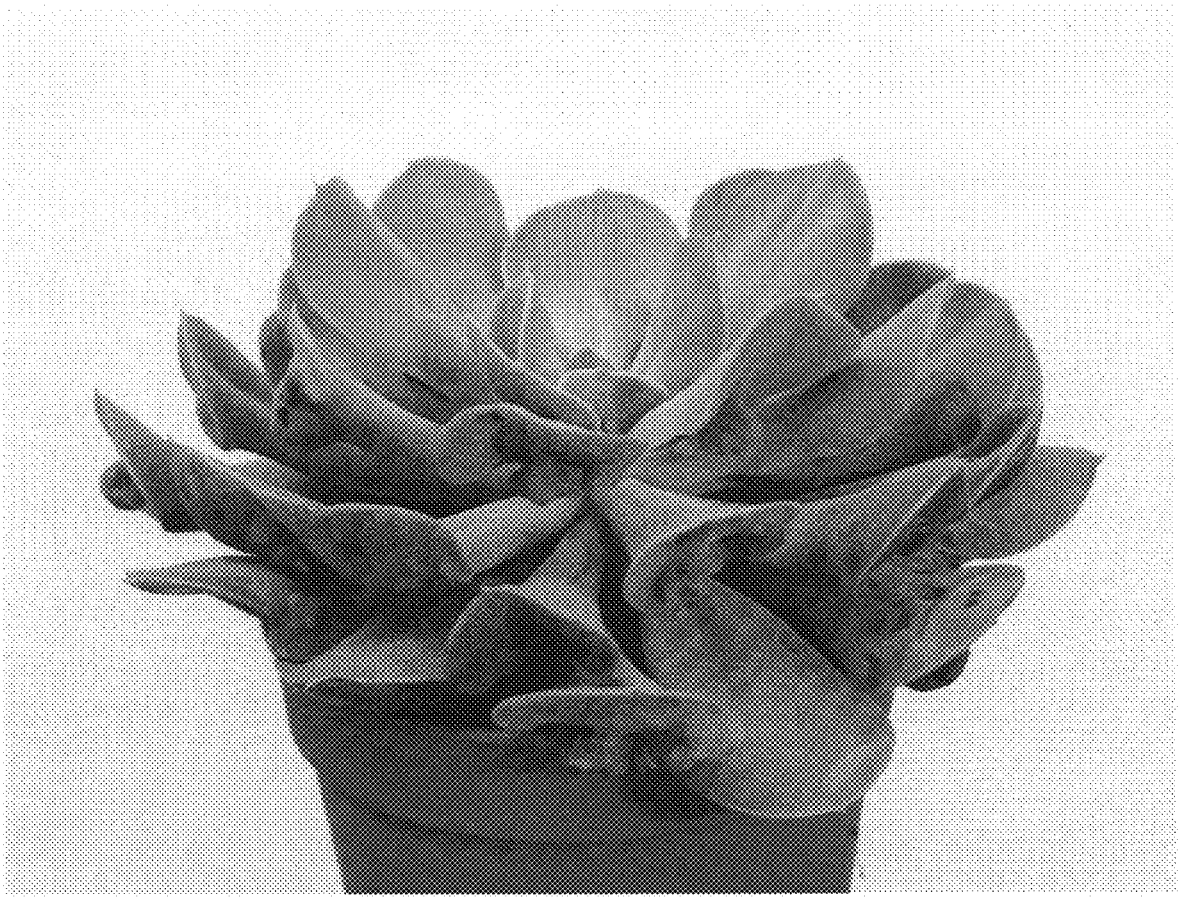
FIG. 1 illustrates, as nearly true as it is reasonably possible to make the same in color photographs of this type, an exemplary plant of 'AMIECH1819' grown in a commercial greenhouse in Heerhugowaard, the Netherlands. This plant is approximately 12 months old, shown planted in a 12.5 cm container.
Figure 2:
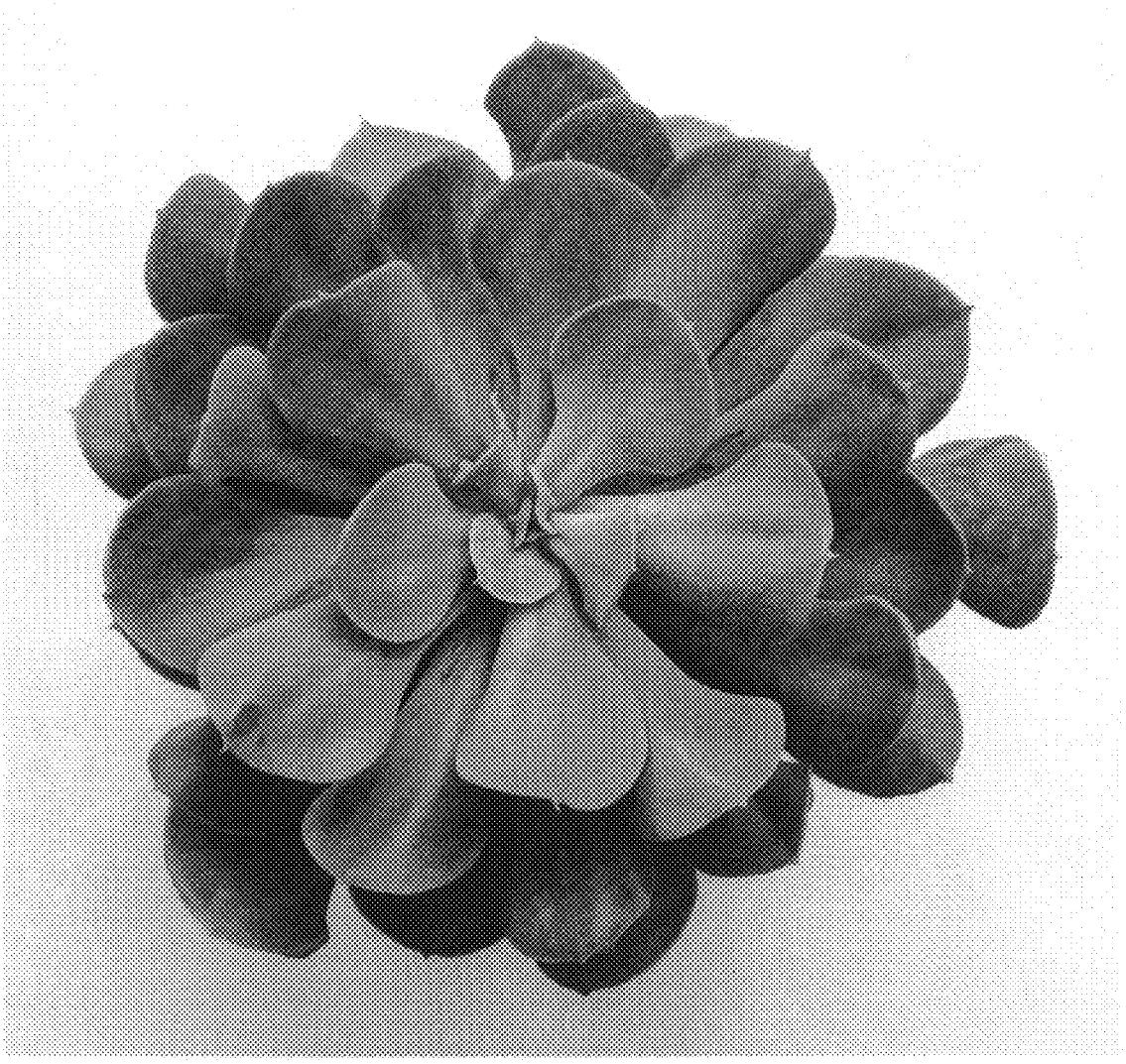
FIG. 2 illustrates, as nearly true as it is reasonably possible to make the same in color photographs of this type, the typical foliage arrangement of 'AMIECH1819'.
Figure 3:
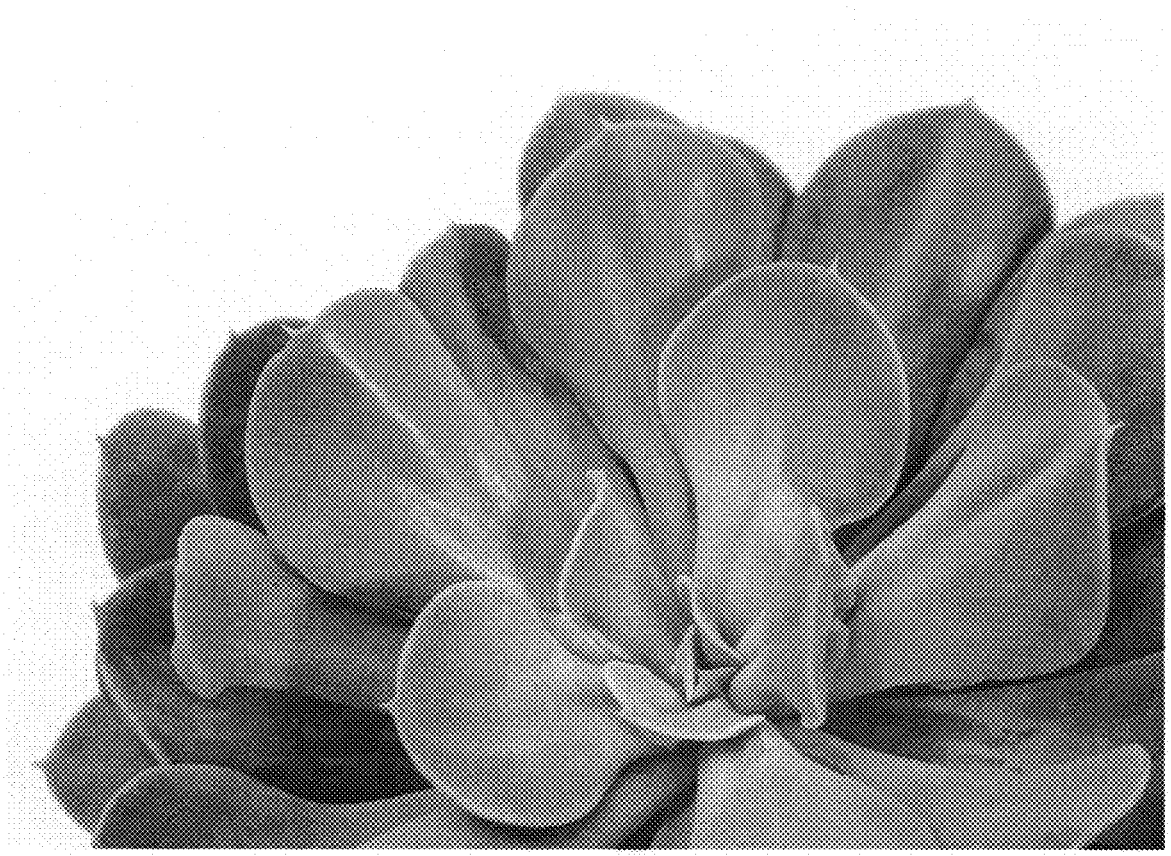
FIG. 3 illustrates, as nearly true as it is reasonably possible to make the same in color photographs of this type, the adaxial surface of the juvenile and mature foliage of 'AMIECH1819'.
Figure 4:
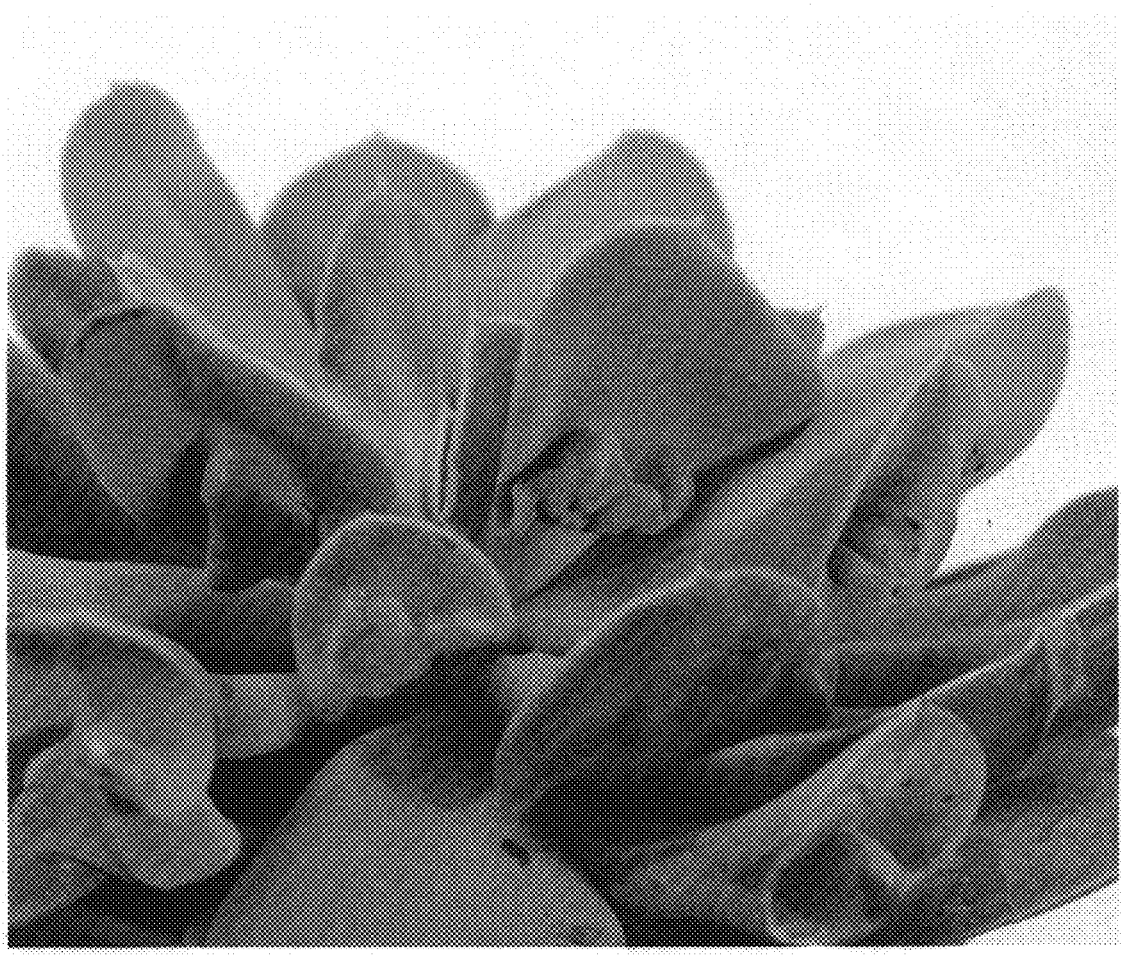
FIG. 4 illustrates, as nearly true as it is reasonably possible to make the same in color photographs of this type, the abaxial surface of the mature foliage of 'AMIECH1819'.

The following observations and measurements made in December of 2018 describe averages from a sample set of six specimens of 12 months old 'AMIECH1819' plants grown in 12.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1819' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH1819' and comparisons with the parent plants and closest known comparator are provided below.

Plant description:

*Growth habit.*—Succulent perennial with foliage growing in a stemless basal rosette.

*Plant shape.*—Flattened.

*Height from soil level to top of foliar plane.*—9.0 cm.

*Plant spread.*—Average of 18.1 cm.

*Growth rate.*—Moderately fast growing.

*Plant vigor.*—Moderately to highly vigorous.

*Propagation.*—Type — Leaf cuttings. Time to initiate rooting — Approximately 21 days at 18 degrees Celsius. Crop time — Approximately 30 weeks to produce a marketable plant in a 10.5 cm container.

*Disease and pest resistance or susceptibility.*—Neither resistance nor susceptibility to typical *Echeveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Foliage:

*Arrangement.*—Rosette.

*Division.*—Simple.

*Attachment.*—Sessile.

*Quantity.*—Approximately 48 leaves per rosette.

*Shape.*—Narrow obovate to near spatulate.

*Dimensions.*—8.3 cm long, 3.6 cm wide, and 1.3 cm thick, on average.

*Aspect.*—Moderately to strongly convex and moderately to strongly revolute to near-tubular; foliage is slightly curved upwards.

*Attitude.*—Juvenile foliage at the center of the rosette is held outward; foliage becomes progressively more relaxed towards the outer whorls of mature foliage, at an average angle of 20 degrees to horizontal.

*Apex.*—Bluntly apiculate.

*Base.*—Long cuneate.

*Margin.*—Entire; lightly undulated.

*Pubescence, texture and luster of the adaxial surface.*—Glabrous, smooth, and matte; moderately to heavily glaucous.

*Pubescence, texture and luster of the abaxial surface.*—Glabrous, smooth, and matte; moderately to heavily glaucous.

*Color.*—Juvenile foliage, adaxial surface — Greyed-green, nearest to RHS 194A, and transitioning to red-purple towards the base, nearest to RHS 65C; lightly suffused with brown, RHS 200B, towards the apex; margins at the base and along the proximal end are yellow-green, RHS 145B, and transition to greyed-red towards the distal end and apex, nearest to RHS 182B; the epicuticular glaucous wax covering the leaf surface is black, nearest to RHS 202B. Juvenile foliage, abaxial surface — Greyed-purple, nearest to RHS 183B, and transitioning to red-purple towards the base, nearest to a mixture of RHS 63B, 63C, and 63D; very lightly suffused with brown, RHS 200B, towards the apex; margins at the base and along the proximal end are yellow-green, RHS 145B, and transition to greyed-red towards the distal end and apex, nearest to RHS 182B; the epicuticular glaucous wax covering the leaf surface is black, nearest to RHS 202B. Mature foliage, adaxial surface — Nearest to in between yellow-green and greyed-green, RHS 148A and 191A; lightly suffused with red-purple towards the base, nearest to RHS 63D; lightly suffused with brown towards the apex, nearest to RHS 200C; margined greyed-brown, nearest to RHS 199B; the epicuticular glaucous wax covering the leaf surface is black, nearest to RHS 202B. Mature foliage, abaxial surface — Yellow-green, nearest to RHS 147A; suffused with red-purple towards the base, nearest to RHS 63C; lightly to heavily suffused with a mixture of greyed-purple and brown towards the apex, nearest to RHS N186C and 200B; margined greyed-brown, nearest to RHS 199B; the epicuticular glaucous wax covering the leaf surface is black, nearest to RHS 202B.

*Venation.*—No venation is visible.

*Petiole.*—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIECH1819' differ from the parent, *Echeveria* hybrid 'Perle von Nurnberg' (not patented), in the following characteristics described in Table 1 below.

TABLE 1

| Characteristic | 'AMIECH1819' | 'Perle von Nurnberg' |
|---|---|---|
| Foliage aspect. | Moderately to strongly convex and moderately to strongly revolute to near-tubular; foliage is slightly curved upwards. | Slightly carinate and slightly concave. |
| Presence of irregularly globular growths on the foliage. | Present. | Not present. |
| Foliage strength at thepoint of attachment. | More strongly held. | More weakly held. |

COMPARISONS WITH THE CLOSEST KNOWN COMPARATOR

Plants of the new cultivar 'AMIECH1819' differ from the closest known commercial comparator, the common form of *Echeveria* sp. 'Topsy Turvy' (not patented), in the following characteristics described in Table 2 below.

TABLE 2

| Characteristic | 'AMIECH1819' | 'Topsy Turvy' |
|---|---|---|
| Growth habit. | Foliage is held more loosely in the rosette. | Foliage is more tightly held in the rosette. |
| Foliage aspect. | Moderately to strongly convex and moderately to strongly revolute to near-tubular; foliage is slightly curved upwards. | Strongly inversely-carinate and strongly revolute. |
| Presence of irregularly globular growths on the foliage. | Present. | Not present. |
| General coloration of the foliage. | Generally appearing to be centered mauve and transitioning to greyed-green towards outer whorls of the rosette. | Generally appearing as pale blue-gray. |

That which is claimed is:

1. A new and distinct variety of *Echeveria* plant named 'AMIECH1819', substantially as described and illustrated herein.

* * * * *